(12) United States Patent
Hall

(10) Patent No.: US 7,833,190 B1
(45) Date of Patent: Nov. 16, 2010

(54) BREAST PUMP

(76) Inventor: Petisamaria Hall, 89 Tickie Ridge Cir., Crawfordville, FL (US) 32327

(*) Notice: Subject to any disclaimer, the term of this patent is extended or adjusted under 35 U.S.C. 154(b) by 133 days.

(21) Appl. No.: 12/120,781

(22) Filed: May 15, 2008

Related U.S. Application Data

(60) Provisional application No. 60/930,503, filed on May 17, 2007.

(51) Int. Cl.
*A61M 1/06* (2006.01)

(52) U.S. Cl. ........................................ 604/74

(58) Field of Classification Search ............. 604/74–76, 604/131, 151, 315; 119/14.42, 14.43, 14.47–14.53; 450/36–37
See application file for complete search history.

(56) References Cited

U.S. PATENT DOCUMENTS

| | | | | |
|---|---|---|---|---|
| 5,616,125 A | * | 4/1997 | Jelks | 604/74 |
| 5,776,098 A | * | 7/1998 | Silver et al. | 604/74 |
| 6,257,847 B1 | * | 7/2001 | Silver et al. | 417/415 |
| 6,379,327 B2 | * | 4/2002 | Lundy | 604/74 |
| 6,440,100 B1 | * | 8/2002 | Prentiss | 604/74 |
| 6,699,213 B1 | * | 3/2004 | Annis et al. | 604/74 |
| 6,702,167 B2 | * | 3/2004 | Annis | 224/576 |
| 2006/0007017 A1 | * | 1/2006 | Mann et al. | 340/870.07 |
| 2006/0106334 A1 | * | 5/2006 | Jordan et al. | 604/74 |
| 2006/0270973 A1 | * | 11/2006 | Chu | 604/74 |

* cited by examiner

*Primary Examiner*—Theodore J Stigell
(74) *Attorney, Agent, or Firm*—Kenneth L Tolar

(57) ABSTRACT

The present invention relates to a breast pump including a cylindrical housing encapsulated by an insulated thermal layer; the housing includes an outer wall and an open top in communication with an interior chamber. Superimposed on the open top is a removable pump assembly having a pair of outlet tubes extending therefrom. At a distal end of each tube is a conical suction cup for placing over a nursing mother's breast nipple. Any one of a plurality of varying sized auxiliary containers, such as a conventional baby bottle, can be placed within the interior chamber to receive and store breast milk extracted from the breasts.

7 Claims, 2 Drawing Sheets

BREAST PUMP

CROSS REFERENCE TO RELATED APPLICATIONS

This application is entitled to the benefit of provisional application No. 60/930,503 filed on May 17, 2007, the specification of which is incorporated herein by reference.

BACKGROUND OF THE INVENTION

The present invention relates to a breast pump that allows a nursing mother to discreetly and efficiently pump breast milk into an auxiliary container.

DESCRIPTION OF THE PRIOR ART

Many nursing mothers prefer to store breast milk so that it is readily available when needed. Conventional breast pumps exist in the art that allow a mother to manually pump breast milk into an auxiliary container. However, in addition to being laborious, the conventional pumps require the mother to partially expose her breasts, which can be embarrassing. Accordingly, there is currently a need for a breast pump that eliminates the aforementioned disadvantages associated with conventional breast pumps. The present invention satisfies this need by providing an automated breast pump that allows a mother to discreetly pump breast milk into an auxiliary container for later use.

SUMMARY OF THE INVENTION

The present invention relates to a breast pump including a cylindrical housing encapsulated by an insulated thermal layer; the housing includes an outer wall and an open top in communication with an interior chamber. Superimposed on the open top is a removable pump assembly including a pair of pumps received within a disc-shaped casing and a pair of outlet tubes extending therefrom. At a distal end of each tube is a conical suction cup for placing over a nursing mother's breast nipple. Any one of a plurality of varying sized auxiliary containers, such as a conventional baby bottle, can be placed within the interior chamber to receive and store breast milk extracted from the breasts. The breast pump further including a means for selectively activating either of said pumps, wherein said means for selectively activating either of said pumps includes a pair of buttons positioned on an exterior surface of said casing, each of said buttons activating one of said pumps thereby allowing a nursing mother to selectively pump either of two breasts.

It is therefore an object of the present invention to provide a breast pump that eliminates the labor and embarrassment associated with the use of conventional breast pumps.

It is another object of the present invention to provide a breast pump that allows a nursing mother to discreetly and automatically pump breast milk from either or both breasts.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
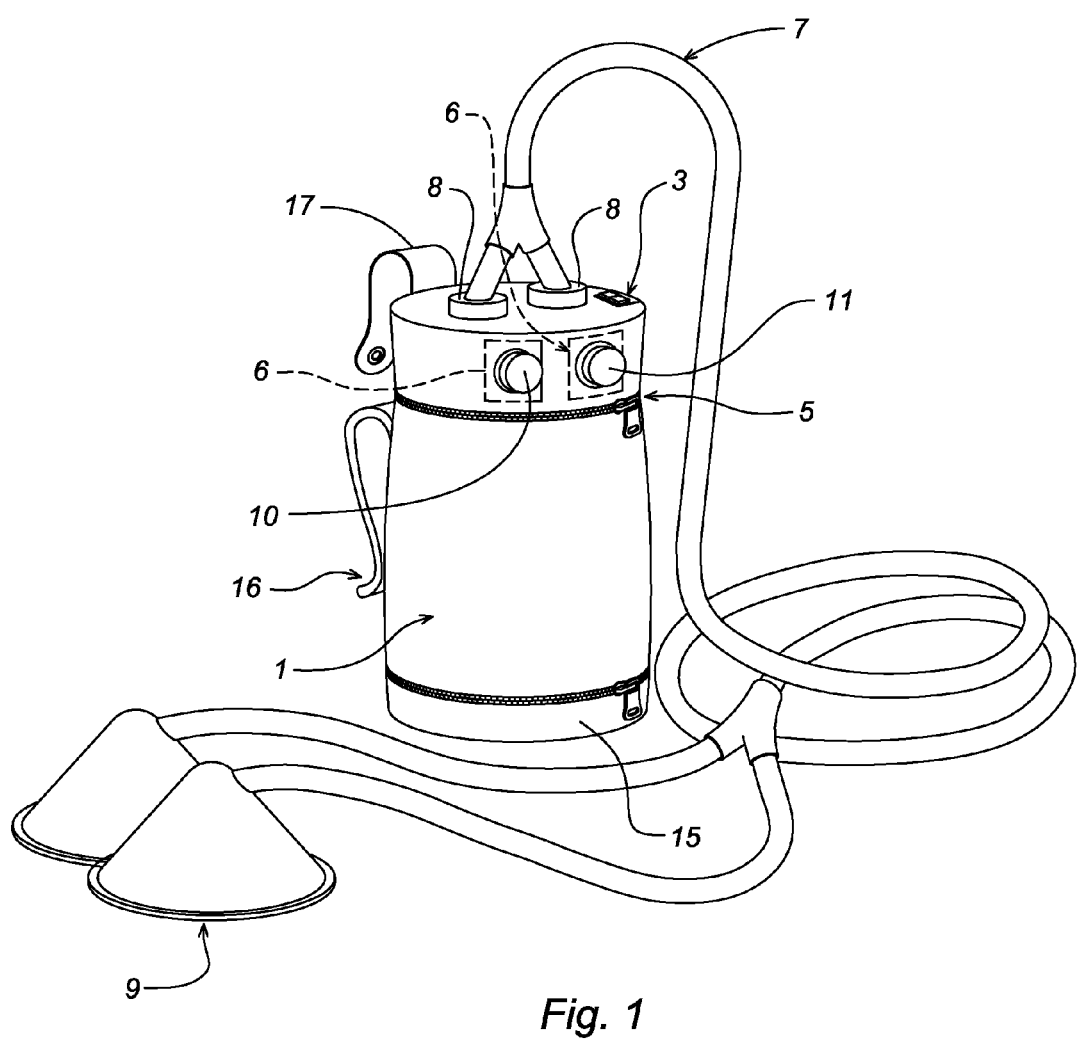
FIG. 1 depicts the breast pump according to the present invention.
Figure 2:
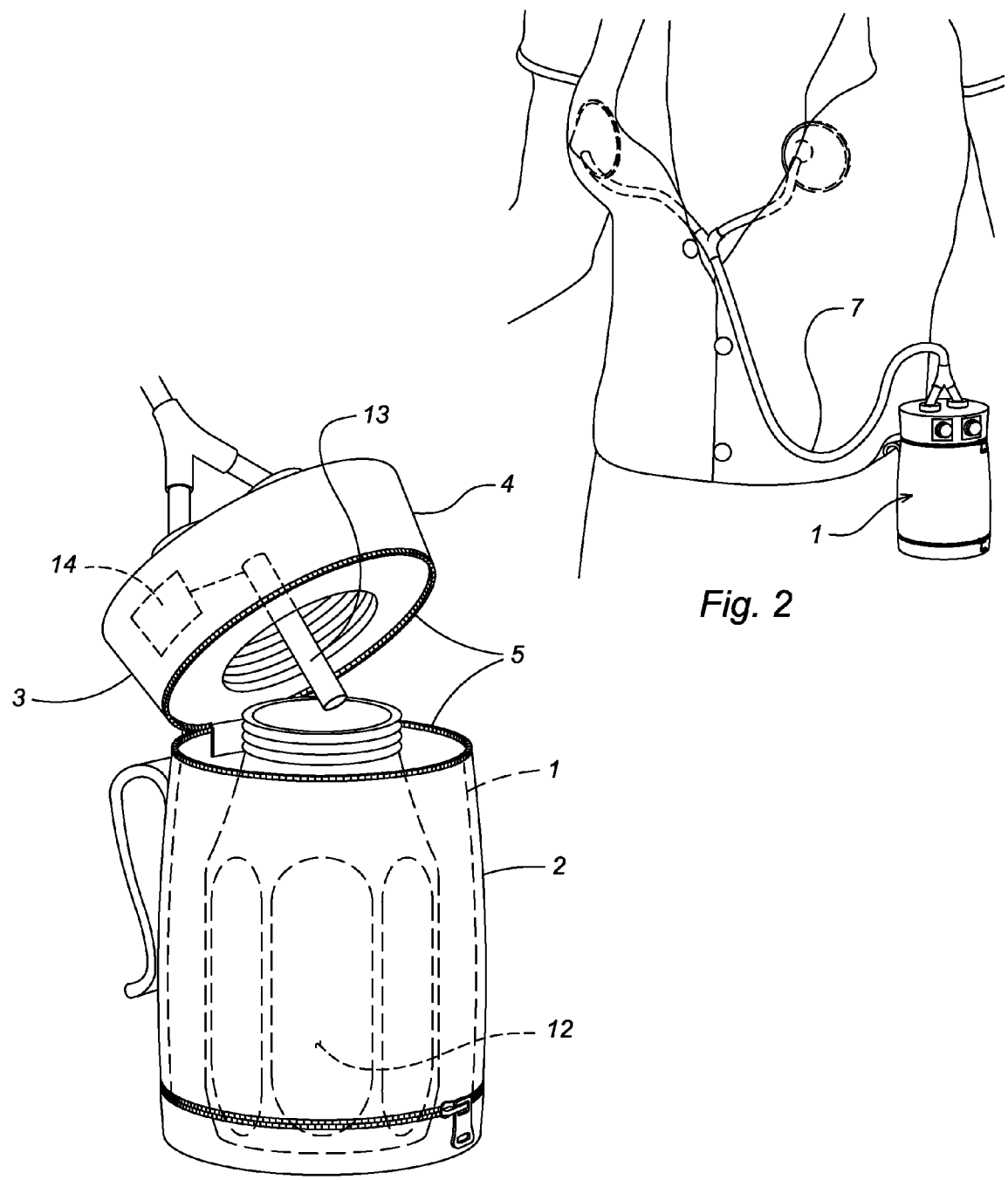
FIG. 2 depicts the breast pump of FIG. 1 secured to a nursing mother.
Figure 3:
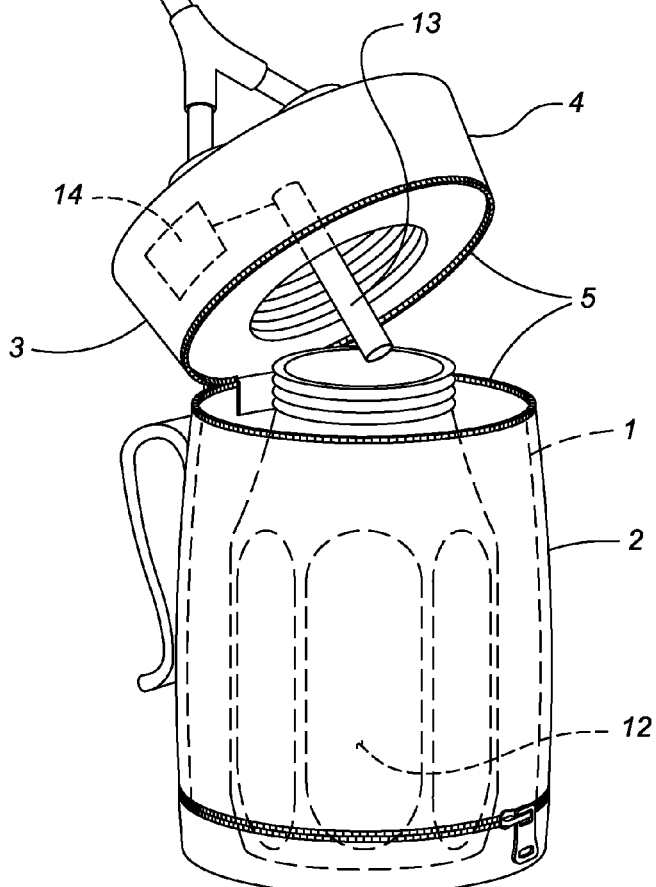
FIG. 3 depicts the breast pump with the pump assembly casing detached from the housing to provide access to the auxiliary container.

A breast pump includes a cylindrical housing 1 encapsulated by an insulated thermal layer 2 having an outer wall and an open top in communication with an interior chamber. Superimposed on the open top is a pump assembly 3 including a disc-shaped casing 4 that is removably securable to the container with a circumferential zipper 5. Received within the casing are a pair of pumps 6 each having an outlet tube 7 connected to the suction side thereof. Each outlet tube passes through a designated port 8 on the top surface of the pump assembly casing; preferably, the outlet tubes are joined at their intermediate sections so as to be more easily concealed and secured. The distal ends of the tubes separate and terminate at a conical suction cup 9 for placing over the breast nipple.

Each internally disposed pump is activated with one of a pair of buttons positioned on the casing exterior. Depressing a first button 10 will activate one of the pumps to extract breast milk from one of the nursing mother's breasts, while depressing a second button 11 will activate the other pump to extract breast milk from the other breast. Accordingly, the mother can elect to pump either or both breasts, as needed.

Any one of a plurality of varying sized auxiliary containers, such as a conventional baby bottle 12, can be placed within the interior chamber. A level sensor 13 extends from the lower surface of the pump assembly casing into the auxiliary container when the casing is properly secured. The sensor is electrically connected to an internally disposed vibrator 14 so that when breast milk reaches a predetermined level within the auxiliary container, the vibrator is activated to alert the nursing mother that the container is full and that the pump(s) can be deactivated.

At the lower end of the housing is a zippered panel 15 that can be detached to remove and install the auxiliary container. On the outer wall is a belt clip 16 and a separable security loop 17 that allow the mother to secure the device to a belt or garment so that the hands are free to perform other tasks.

The above described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The invention claimed is:
1. A breast pump comprising:
    a housing encapsulated by an insulated thermal layer, said housing having an outer wall and an open top in communication with an interior chamber;
    an auxiliary container received within said interior chamber, the auxiliary container configured to receive breast milk;
    a disc-shaped casing superimposed on the open top of said housing, said casing including a circumferential zipper for removably securing said casing to the open top of said housing;

a pair of pumps received within the casing, each of said pumps having an outlet tube connected to a suction side thereof;

a conical suction cup at a distal end of each of said outlet tubes for placing over a breast nipple;

means for selectively activating either of said pumps, the means located on the casing.

2. The breast pump according to claim 1 wherein said means for selectively activating either of said pumps includes a pair of buttons positioned on an exterior surface of said casing, each of said buttons activating one of said pumps thereby allowing a nursing mother to selectively pump either of two breasts.

3. The breast pump according claim 2 further comprising a level sensor extending from a lower surface of the casing and into the auxiliary container when the casing is secured to said housing, said sensor electrically connected to an internally-disposed vibrator so that when breast milk reaches a predetermined level within the auxiliary container, the vibrator is activated to alert a nursing mother that the auxiliary container is full and that the pumps should be deactivated.

4. The breast pump according claim 3 further comprising a zippered, detachable panel at a lower end of the housing that provides selective access to the auxiliary container.

5. The breast pump according claim 4 further comprising a belt clip and a separable security loop on the outer wall of said housing that allow the nursing mother to secure the breast pump to a garment.

6. The breast pump according claim 5 wherein said housing is cylindrical.

7. The breast pump according claim 6 wherein the outlet tube of one of said pumps is coupled with the outlet tube of another of said pumps.

* * * * *